United States Patent [19]

Garlich et al.

[11] Patent Number: 5,286,479
[45] Date of Patent: Feb. 15, 1994

[54] ORAL COMPOSITIONS FOR SUPPRESSING MOUTH ODORS

[75] Inventors: Joseph R. Garlich; Tipton T. Masterson, both of Lake Jackson; Jaime Simon, Angleton, all of Tex.; Vidyadhar B. Hegde, Indianapolis, Ind.

[73] Assignee: The Dow Chemical Company, Midland, Mich.

[21] Appl. No.: 805,599

[22] Filed: Dec. 10, 1991

[51] Int. Cl.$^5$ .......................... A61K 7/16; A61K 7/22
[52] U.S. Cl. ........................................... 424/54; 424/49
[58] Field of Search ..................................... 424/49-58

[56] References Cited

U.S. PATENT DOCUMENTS

| | | |
|---|---|---|
| 3,044,939 | 7/1962 | Scanlan et al. . |
| 3,934,002 | 1/1976 | Haefele . |
| 4,039,653 | 8/1977 | DeFoney et al. . |
| 4,041,149 | 8/1977 | Gaffar et al. . |
| 4,138,477 | 2/1979 | Gaffar . |
| 4,193,988 | 3/1980 | Forward et al. . |
| 4,259,316 | 3/1981 | Nakashima et al. . |
| 4,263,276 | 4/1981 | Harvey . |
| 4,267,166 | 5/1981 | Yajima . |
| 4,305,928 | 12/1981 | Harvey . |
| 4,332,791 | 6/1982 | Raaf et al. . |
| 4,335,102 | 6/1982 | Nakashima et al. . |
| 4,339,429 | 7/1982 | Raaf et al. ............................ 424/49 |
| 4,394,371 | 7/1983 | Barberio . |
| 4,430,323 | 2/1984 | Silver . |
| 4,469,674 | 9/1984 | Shah et al. . |
| 4,472,373 | 8/1984 | Ryan . |
| 4,512,968 | 4/1985 | Komiyama et al. . |
| 4,525,342 | 6/1985 | Weiss et al. . |
| 4,528,181 | 7/1985 | Morton et al. . |
| 4,597,959 | 7/1986 | Barr . |
| 4,622,220 | 11/1986 | Frosch .................................. 424/49 |
| 4,626,427 | 12/1986 | Wienecke et al. . |
| 4,645,662 | 2/1987 | Nakashima et al. . |
| 4,689,214 | 8/1987 | Niles et al. . |
| 4,689,215 | 8/1987 | Ratcliff . |
| 4,719,100 | 1/1988 | Frosch .................................. 424/49 |
| 4,740,368 | 4/1988 | Plevy . |
| 4,775,725 | 10/1988 | DePasquale . |
| 4,795,628 | 1/1989 | Afseth .................................. 424/49 |
| 4,814,163 | 3/1989 | Barth . |
| 4,814,164 | 3/1989 | Barth et al. . |
| 4,824,661 | 4/1989 | Wagner ................................ 424/49 |
| 4,826,675 | 5/1989 | Gaffar et al. . |
| 4,837,009 | 6/1989 | Ratcliff . |
| 4,997,640 | 3/1991 | Bird et al. ............................ 424/49 |
| 5,037,633 | 8/1991 | Ziemkiewicz et al. ............... 424/49 |
| 5,037,634 | 8/1991 | Williams et al. . |
| 5,094,842 | 3/1992 | Riley .................................... 424/52 |

FOREIGN PATENT DOCUMENTS

| | | |
|---|---|---|
| 0161898 | 11/1985 | European Pat. Off. . |
| 321180A1 | 6/1989 | European Pat. Off. . |
| 2918134 | 11/1979 | Fed. Rep. of Germany . |
| 61-200908 | 9/1986 | Japan . |
| 1384375 | 2/1975 | United Kingdom . |

OTHER PUBLICATIONS

Yaegaki and Suetaka, "The Effect of Zinc Chloride Mouthwash on the Production of Oral Malodour, the Degradations of Salivary Cellular Elements, and Proteins", *J. Dental Health*, 39, 377-386 (1989).

H. Nordbo, "The Affinity of Chlorhexidine for Hydroxyapatite and Tooth Surfaces", *Scan. J. Dent. Res.*, 80, 465-473 (1972).

(List continued on next page.)

*Primary Examiner*—Shep K. Rose

[57] ABSTRACT

An oral composition for suppressing mouth odors comprising from about 0.001 to about 10 percent by weight of a copper salt and from about 0.001 to about 10 percent by weight phytic acid or a physiologically acceptable salt thereof. A cationic antimicrobial compound is added to the oral composition to aid in the prevention of plaque formation and gingivitis provided the oral composition contains from about 0.01 to about 20 percent by weight of a compatibilizing agent.

31 Claims, No Drawings

OTHER PUBLICATIONS

H. Nordbo and G. Rolla, "Desorption of Salivary Proteins from Hydroxyapatite by Phytic Acid and Glycerophosphate and the Plaque-Inhibiting Effect of the Two Compounds In Vivo", *J. Dent. Res.*, 51, 800–802 (1972).

D. S. Magrill, "The Effect of pH and of Orthophosphate on the Adsorption of Phytate by Hydroxyapatite During Prolonged Exposure", *Archs oral Biol.*, 18, 1269–1273 (1973).

H. W. Kaufman and I. Kleinberg, "X-Ray Diffraction Study of the Effect of Phytate on the In Vitro Formation of Calcium Phosphates", *J. Dent. Res.*, 52 (Special Issue), 169 (1973).

A. Gaffar and N. Rustogi, "Effects of Sodium Phytate and Benzethonium Chloride Rinses on Plaque Formation in Humans", *Caries Res.*, 16, 472–474 (1982).

H. Nordbo and G. Rolla, "The Plaque-Inhibiting Capacity of Glycerophosphate and Phytic Acid", *J. Dent. Res.*, 79, 507–509 (1971).

T. H. Grenby, "Trials of Three Organic Phosphorus-Containing Compounds as Protective Agents Against Dental Caries in Rats", *J. Dent. Res.*, 52, 454–461 (1973).

M. F. Cole and W. H. Bowen, "Effect of Sodium Phytate on the Chemical and Microbial Composition of Dental Plaque in the Monkey", *J. Dent. Res.*, 54, 449–457 (1975).

ORAL COMPOSITIONS FOR SUPPRESSING MOUTH ODORS

BACKGROUND OF THE INVENTION

The present invention relates to oral compositions for the control of volatile compounds associated with oral malodor.

"Oral composition" means a composition for topical applications to the oral cavity to clean and care for the teeth as well as the oral cavity surfaces. Representatives of such compositions are oral hygiene products and dentifrices such as mouthwashes or rinses, toothpaste, dental gels, tooth powder, chewing gum, lozenges, and similar products. In addition to cleaning teeth to remove dental plaque, the function of oral hygiene preparations is to stop the formation of dental calculus, to prevent dental disorders such as caries, periodontitis and gingivitis, and also to eliminate halitosis.

Dental plaque is a deposit which forms on teeth and consists of inorganic and organic components derived from saliva, food and bacteria which are present in the oral cavity. When plaque undergoes calcification it forms dental calculus, or tartar as it is sometimes called. Dental calculus is largely calcium and orthophosphate arranged in a crystal lattice called hydroxyapatite (HAP).

Oral malodor, or halitosis, is caused by the putrefactive activity of microorganisms on appropriate substrate components of dental plaque, debris adhering to mucous membranes and salivary cellular elements to produce volatile sulfur compounds. These sulfur volatiles primarily consists of hydrogen sulfide ($H_2S$), methyl mercaptan ($CH_3SH$) and traces of dimethyl sulfide ($(CH_3)_2S$). Volatile sulfur compounds, aromatic amines, ammonia and urea have also been shown to increase in the mouth of patients suffering from periodontal disease, see, for example, J. Periodontal Res., 15, 185–192 (1980), Clin. Chem., 27, 842–845 (1981), Intl. Den. J. 28, 309–319 (1978).

Methods of inhibiting volatile sulfur compounds to reduce the production of mouth odor have included the use of dentifrices containing antimicrobials, such as, chlorhexidine. However, the side effects associated with chlorhexidine, such as a bitter taste and staining of the teeth, tongue, gums and oral mucosa, precludes the use of chlorhexidine in oral compositions.

Copper compounds including copper chlorophyllin, copper gluconate, copper citrate and copper long chain alkyloyl sarcosine have been used to reduce mouth odors. See, for example, U.S. Pat. Nos. 3,044,939; 3,565,933 and 4,112,066 and Nippon Shishyubyo Gakkai Kaishi, 490–498 (1981) for oral compositions containing such compounds. These copper compounds, however, do not fully exert their mouth odor reducing effect when blended in relatively small amounts. As copper is astringent, the amount of these copper compounds required to assure their effect in reducing mouth odor makes such oral compositions unpleasant in taste.

An oral composition containing copper gluconate, a fluorine compound, and an alkali metal salt of an alkyl sulfate having 8 to 18 carbon atoms is reported in published European Patent Application 0321180. It was reported that these components act in a synergistic manner so that mouth odor suppression is accomplished when each ingredient is contained in a low concentration.

While the use of copper compounds in oral compositions for controlling mouth malodor is known, none of the references provide a means by which the copper can be retained in the oral cavity to control mouth odor over a period of time. In addition, many copper compounds are unstable at biological pH (about 7.0) resulting in undesirable cloudiness and precipitation of insoluble by-products.

It is therefore desirable when using copper in an oral composition to control mouth malodor, to have an oral composition in which the copper compound is effective at a relatively low concentration, can be maintained in the oral cavity over a prolonged period of time, and remains soluble when used in liquid compositions. It would also be desirable to prepare an oral composition capable of controlling mouth malodor in addition to the prevention of plaque and calculus formation.

SUMMARY OF THE INVENTION

The present invention relates to oral compositions for controlling mouth malodor comprising an oral composition consisting essentially of an orally-acceptable vehicle containing therein: (a) from about 0.0002 to about 1 percent by weight of one or more copper salts; (2) from about 0.001 to about 10 percent by weight of one or more compounds having C-O-P bonds wherein the compound having C-O-P bonds is myo-inositol hexakis(dihydrogen phosphate), myo-inositol tetrakis(dihydrogen phosphate), myo-inositol pentakis(dihydrogen phosphate) or physiologically acceptable salts thereof; (3) from about 0.001 to about 10 percent by weight of at least one cationic antimicrobial compound; and (4) from about 0.1 to about 20 percent by weight of a compatibilizing agent.

The addition of the quaternary ammonium compound reduces the amount of bacteria which are responsible for production of volatile sulfur compounds. The inclusion of a quaternary ammonium compound also aids in reducing the formation of dental plaque and/or gingivitis and/or periodontitis and/or dental caries.

It has also been found that the addition of phytic acid to a liquid composition containing a copper (II) salt prevents the undesirable cloudiness and precipitation of insoluble by-products associated with the instability of copper compounds at about pH 7.2

DETAILED DESCRIPTION OF THE INVENTION

The oral compositions of the present invention provide for improved mouth malodor suppression by combining in an orally-acceptable vehicle at least one copper (II) salt and phytic acid or derivatives thereof. In the presence of a compatibilizing agent, the oral composition can also contain an antimicrobial agent for killing bacteria in the oral cavity thereby reducing the level of plaque and/or gingivitis formed along with mouth malodor suppression. An "orally-acceptable vehicle" means a medium in which the copper (II) salt and phytic acid may be administered to the oral cavity surfaces without substantial harmful effects to the surfaces thereof and also is pleasant in taste. As used herein, the term "copper" refers to the cupric ion.

To enhance the control of mouth malodor by copper salts, it has been unexpectedly found that the retention of the copper ion within the oral cavity can be substantially enhanced if the copper salt is used in combination with a hydroxyapatite seeking agent, such as phytic acid or a derivative thereof. The ability of the copper to remain in contact with the tooth surface is referred to as the "substantivity" of the agent. It has now also been unexpectedly found that in the presence of a compatibilizing agent, in addition to the copper salt and phytic acid, a cationic antimicrobial compound can be added to the oral composition to control dental plaque, gingivitis, periodontitis and oral malodor without the components precipitating.

Copper compounds useful in the present invention are any copper salt, or combination thereof, which has a stability constant less than that of copper phytate, such as, copper acetate, copper gluconate, copper sulfate, copper chloride, and the like. Other copper compounds useful in the present invention include copper succinate and copper tartrate. The preferred copper salts are copper acetate and copper gluconate. The copper salts are preferably present in the oral composition of the present invention in an amount of from about 0.0002 to about 1 percent by weight of the total composition, preferably from about 0.0002 to about 0.5 percent by weight.

The tooth surface seeking agent of the present invention are compounds which contain a carbon atom covalently bonded to an oxygen atom, the oxygen being covalently bonded to a phosphate atom, hereinafter referred to as C-O-P bonds. The compounds of the present invention which contain C-O-P bonds are phosphate esters of myo-inositol, such as phytic acid, also known as myo-inositol hexakis(dihydrogen phosphate), inositol hexaphosphoric acid, and 1,2,3,4,5,6-cyclohexanehexolphosphoric acid. As used herein "phytic acid" means the hexakis phosphate ester of myo-inositol, myo-inositol hexakis(dihydrogen phosphate) and the lesser substituted tetrakis and pentakis phosphate esters of myo-inositol, myo-inositol tetrakis(dihydrogen phosphate) and myo-inositol pentakis(dihydrogen phosphate) respectively, and physiologically acceptable salts thereof, such as alkali metal, alkaline earth metal, ammonium salts or mixtures thereof. Phytin, which is the calcium magnesium salt of phytic acid, represented by the formula $Ca_5Mg(C_6H_{12}O_{24}P_6 \cdot 3H_2O)_2$, can also be used in the present invention in addition to or for replacement of the phytic acid. These phytic acid compounds may be used singly or in combination.

Phytic acid is present in the oral composition of the present invention in an amount of from about 0.001 to about 10 percent by weight of the total composition. When the oral composition is essentially liquid in nature, the phytic acid or salt thereof is typically present in an amount of from about 0.005 to about 5 percent, and preferably from about 0.01 to about 1 percent by weight.

The molar ratio of cupric ion to phytic acid in the oral composition of the present invention is from about 1:100 to about 1:1, preferably from about 1:50 to about 1:1 and more preferably about 1:20 to about 1:1.

In certain preferred forms of the invention, the composition is substantially liquid in character, such as a mouthwash or rinse. In such a preparation the vehicle can be water or a water-alcohol mixture. When alcohol is used in the mixture, the weight ratio of water to alcohol is generally in the range of from about 1:1 to about 20:1, preferably from about 3:1 to 10:1 and more preferably from about 4:1 to about 6:1. The total amount of water-buffer or water-alcohol mixture in this type of preparation is typically in the range of from about 70 percent to about 99.9 percent by weight of the preparation.

The pH of such liquid and other preparations of the invention is generally in the range of from about 4.5 to about 9, and preferably from about 5.5 to about 8, more preferably in the range of from about 6 to about 8.

In certain other desirable forms of this invention, the oral composition may be substantially solid or semisolid in character, such as toothpowder, a dental tablet, a toothpaste, gel or dental cream. The vehicle of such solid or semisolid oral preparation generally contains added polishing material more fully described hereinafter.

To aid in the prevention of dental plaque and/or gingivitis as well as controlling oral malodor, the oral composition of the present invention can contain one or more cationic antimicrobial compounds. As used herein, a "cationic antimicrobial compound" refers to an organic amine where the nitrogen is capable of being positively charged in an aqueous environment, and is represented by one or more of the following general formulae from A-J:

(A) Quaternary ammonium compounds represented by formula I

or formula II

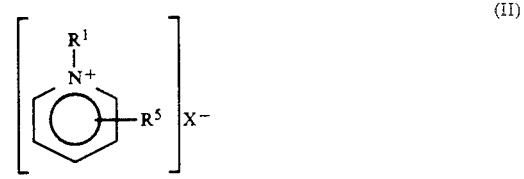

wherein:

$R^1$ is a $C_8$-$C_{20}$ alkyl;

$R^2$ is benzyl or $C_1$-$C_{12}$ alkyl;

$R^3$ and $R^4$ are independently a $C_1$-$C_7$ alkyl or -$(CH_2$—$CH_2$—$O)_n$H wherein n is an integer from 1 to 6;

$R^5$ is -H, a $C_1$-$C_7$ alkyl or -$(CH_2$-$CHOH$-$CH_2$-$O)_n$H wherein n is an integer from 1 to 6; and $X^-$ is chloride ($Cl^-$), bromide ($Br^-$), iodide ($I^-$) or fluoride ($F^-$);

(B) Pyridinium chlorides containing alkylthiomethyl or alkoxymethyl hydrophobic groups as disclosed by Weglowski et al., J. Phar. Sci., 80, 91-85 (1991), the disclosure of which is hereby incorporated by reference, having the formula

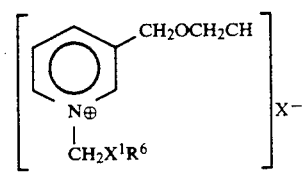

wherein X is as defined herein before and $X^1$ is oxygen or sulfur; and $R^6$ is a $C_4$-$C_{16}$ alkyl or benzyl;

(C) Quaternary ammonium compounds that are esters of betaine and fatty alcohols, as disclosed by Linstedt et al., Antimicrobial Agents and Chemotherapy, 39, 1949-1954 (1990), the disclosure of which is hereby incorporated by reference, having the formula

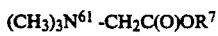

$(CH_3)_3N^{\oplus}-CH_2C(O)OR^7$ wherein $R^7$ is a $C_{10}-C_{18}$ alkyl; and physiologically acceptable salts thereof;

(D) Sanguinarine and sanguinaria, sanguinaria being an extract from the bloodroot plant *Sanguinaria canadensis*, the extract containing benzophenanthridine alkaloids such as sanguinarine, chelerythrine, protopine, homochelidonine and physiologically acceptable salts thereof as disclosed in U.S. Pat. Nos. 4,145,412 and 4,406,881, the disclosures of which are hereby incorporated by reference, sanguinaria being available in dentifrices under the trademark Viadent™ brand sanguinaria; the major active ingredient sanguinarine chloride salt having the formula

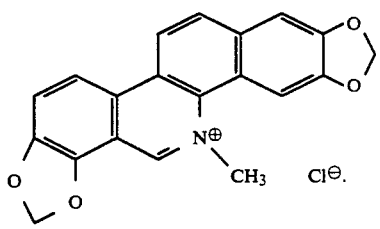

(E) Morpholine compounds as disclosed in U.S. Pat. No. 4,894,221, the disclosure of which is hereby incorporate by reference, the morpholine compounds having the formula

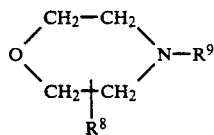

wherein $R^8$ is a $C_8-C_{16}$ alkyl at the 2 or 3 position of the morpholino ring;

$R^9$ is a $C_2-C_{10}$ alkyl substituted with a hydroxy group at other than the alpha-position;

the sum of $R_8$ and $R_9$ being greater than or equal to 10 and preferably 10-20; and physiologically acceptable salts thereof;

(F) Antibacterial secondary amines and amides as disclosed in J. Antibacterial and Antifungal Agents, 17, 371 (1989), the disclosure of which is hereby incorporated by reference, wherein the antibacterial compounds have the following formulae

wherein $R^{10}$ is a $C_{10}-C_{18}$ alkyl;

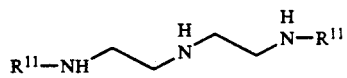

wherein each $R^{11}$ is independently $C_8H_{17}$ or $C_{10}H_{21}$;

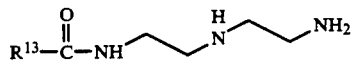

wherein $R^{13}$ is a $C_9-C_{17}$ alkyl;

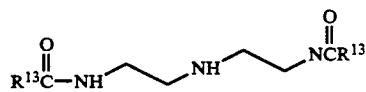

wherein each $R^{13}$ is independently $C_7H_{15}$ or $C_9H_{19}$; and physiologically acceptable salts thereof;

(G) Dialkyl amines and N,N'-dialkylopolymethylenediamines as disclosed in J. Antibacterial and Antifungal Agents, 17; 579 (1989), the disclosure of which is hereby incorporated by reference, having the formula

$R^{14}-NH-R^{14}$ wherein each $R^{14}$ is independently $C_8H_{17}$ or $C_{12}H_{25}$; or formula

$R^{15}-NH(CH_2)_nNH-R^{15}$ wherein each $R^{15}$ is independently a $C_7-C_{10}$ alkyl;

n is an integer from 2 to 5; and physiologically acceptable salts thereof;

(H) N'-Alkyl-N-(2-aminoethyl)piperidine compounds as disclosed by Murata et al., J. Pharm. Sci., 80, 26-28 (1991), the disclosure of which is hereby incorporated by reference, the compounds having the formula

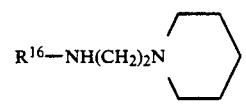

wherein $R^{16}$ is a $C_{10}-C_{18}$ alkyl; and physiologically acceptable salts thereof;

(I) The quaternary ammonium compound 4-(2-propylenepentyl)-1-piperidinoethanol having the structure

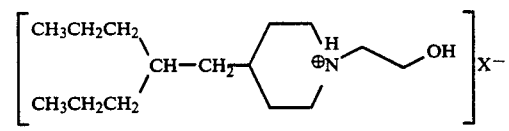

wherein $X^-$ is as defined hereinbefore; described in the literature as Octapinal ™ brand 4-(2-propylenepentyl)-1-piperidinoethanol (Ferrosan AB, Sweden); and (J) Alkyl-N-betaine in combination with an alkyl-N,N-dimethylamine; the alkyl-N-betaine having the structure

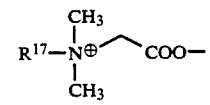

wherein $R^{17}$ is a $C_{10}-C_{18}$ alkyl;

the alkyl-N,N-dimethylamine having the structure

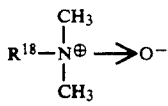

wherein $R^{18}$ is a $C_{10}$–$C_{18}$ alkyl;

as disclosed in U.S. Pat. No. 4,839,158, the disclosure of which is hereby incorporated by reference.

As used herein, the term "alkyl" means a linear or branched alkyl and thus secondary and tertiary alkyls are included. The alkyl terms up to $C_{20}$ include, for example, t-butyl, sec-butyl, isobutyl, and in like manner all such branched or straight chain alkyls.

Preferred quaternary ammonium antibacterial agents include dodecyl trimethyl ammonium bromide, benzyl dimethyl stearyl ammonium chloride, N-tetradecyl-4-ethylpyridinium chloride and cetylpyridinium chloride. The terms antibacterial and antimicrobial mean the ability to inhibit growth, metabolism or reproduction of microorganisms.

The cationic antimicrobial compounds useful in the present invention are commercially available or may be obtained by those of ordinary skill in the art without undue experimentation. For example, quaternary ammonium compounds may be produced by reacting alkyl halides with ammonia or primary amines, or by reacting a tertiary amine, pyridine or pyridine derivative with an alkyl halide. See, for example, Zoltewicz and Deady, Adv. Heterocycl. Chem., 22, 71–121 (1978); U.S. Pat. Nos. 2,446,792; 2,295,504 and 4,994,199, the teachings of which are hereby incorporated by reference.

One or more cationic antimicrobial compounds are employed in amounts such that the oral product contains from about 0.001 to about 10 percent by weight of the antimicrobial compound. Preferably for desired levels of antiplaque and antigingivitis effect, the finished oral product contains from about 0.01 to about 5 percent, and preferably from about 0.025 to 1.0 percent by weight of the antimicrobial compound. Typically a singular antimicrobial compound is employed in the oral product.

When the oral composition is essentially liquid in nature, to maintain the copper ion, phytic acid and cationic antimicrobial compound in solution, it is desirable for the composition to contain a sufficient amount of a compatibilizing agent to keep the phytic acid, copper ion and cationic antimicrobial compound in solution. Compatibilizing agents in the present invention are those which do not have a detrimental effect on the substantivity of the phytic acid, copper ion and cationic antimicrobial compound in solution and maintain the components in solution such that the composition does not visually become turbid after standing for 12 to 15 hours at room temperature.

While not wishing to be bound by theory, it is believed the compatibilizing agents of the present invention reduce the interaction between the phytic acid and cationic antimicrobial compound, reducing or preventing the formation of a precipitate when these two compounds are exposed to each other in an aqueous environment. Particularly useful compatibilizing agents in the present invention are acids and their alkali metal or alkaline-earth metal salts, or mixtures thereof, designated herein as anionic buffers. Suitable anionic buffers are, for example, phosphate, acetate, borate, citrate, bicarbonate, gluconate, tartrate, sulfate, and the like, or mixtures thereof. The preferred anionic buffers being phosphate and/or bicarbonate. The amount of anionic buffer in the oral compositions of the present invention is from about 0.1 to about 20 percent by weight, preferably from about 0.1 to about 10 percent by weight of the total composition. When the oral composition is essentially in the liquid form, the anionic buffer is present in a concentration of about 0.1 M to about 1.0 M, preferably from about 0.25 M to about 0.75 M.

Preparation of the oral compositions of the present invention can be done by using customary procedures for unifying components applied to the teeth and gingiva. It has been found that when the oral compositions of the present invention contain the compatibilizing agent and the cationic antimicrobial compound, in addition to polyvalent metal ions and the phytic acid, the compositions are advantageously prepared by (a) dissolving the metal ion, phytic acid and compatibilizing agent in water, and then (b) adding the cationic antimicrobial compound or cationic antimicrobial solution to the solution obtained from step a. The pH of the oral composition is adjusted to between about 6 and about 8 either before or after the addition of the cationic antimicrobial compound or cationic antimicrobial solution. Other components, such as sweetening and flavoring agents as described more fully herein, can then be added if desired.

The dentifrices of the present invention may also be in a kit form for treating the oral cavity, the kit comprising one or more compounds having C-O-P bonds wherein the compound having C-O-P bonds is myo-inositol hexakis(dihydrogen phosphate), myo-inositol tetrakis(dihydrogen phosphate), myo-inositol pentakis(dihydrogen phosphate) or physiologically acceptable salts thereof; a copper salt, a compatibilizing agent and at least one cationic antimicrobial compound, the compound having C-O-P bonds, copper salt, antimicrobial compound and compatibilizing agent each being in an orally-acceptable vehicle; and a means to contain the compound having C-O-P bonds separately from the cationic antimicrobial. Means to separate the compound having C-O-P bonds and cationic antimicrobial compound include placing them in separate containers or placing them in a compartmentalized container. The copper salt is preferably mixed with the compound having C-O-P bonds; the compatibilizing agent may be mixed with the compound having C-O-P bonds, with the cationic antimicrobial, or is placed in a separate container.

When the dentifrice of the present invention is in a kit form, the separate components (i.e., compound having C-O-P bonds, copper salt, compatibilizing agent and cationic antimicrobial compound) are mixed prior to application.

When mixing the components prior to application to the oral cavity, it may be necessary to increase the concentration of the compounds to account for dilution effects which can occur upon mixing. When applying the compound having C-O-P bonds, copper salt, compatibilizing agent and cationic antimicrobial in a kit form by mixing prior to use, the concentration of the individual compounds to which the oral cavity is exposed should be in the range given hereinbefore for their concentration in the final dentifrice product.

A variety of other ingredients may be added to the dentifrices of the present invention. Thus for example, prophylactic agents, polishing agents, soaps or detergents, flavoring and sweetening agents, thickening agents and humectants may be included using techniques which are know to the art.

Representative prophylactic agents include supplemental caries-preventing materials such as, for example, sodium fluoride, stannous fluoride, potassium fluoride, hexylamine hydrofluoride, myristylamine hydrofluoride, betaine fluoride, glycine potassium fluoride. A particularly preferred fluoride is sodium fluoride. Typically these prophylactic agents are present in sufficient concentrations so as to provide an available fluoride ion concentration of up to about 2 percent by weight, and preferably from about 0.5 percent to about 2 percent by weight, of the dentifrice composition.

Suitable polishing agents include, for example, abrasive materials such as insoluble condensed phosphates such as calcium pyrophosphate, insoluble calcium polyphosphate (also known as calcium polymetaphosphate) and highly polymerized sodium polyphosphate; and water impervious cross-linked thermosetting resins such as the condensation products of melamine and urea with formaldehyde. Other suitable polishing agents will be obvious to those skilled in the art.

The polishing material is generally present in the solid or semisolid compositions in weight concentrations of from about 10 to about 99 percent. Preferably, it is present in amounts ranging from about 20 to about 75 percent in toothpaste, and from about 70 percent to about 99 percent in tooth powder.

Soaps or detergents may also be employed in the present invention to lower the surface tension to achieve increased prophylactic action, assist in achieving thorough and complete dispersion of the anticalculus agent and render the instant compositions more cosmetically acceptable. Suitable soaps include, for example, the soaps of high molecular weight fatty acids such as sodium and potassium soaps of myristic, stearic or palmitic acids and fatty acids mixtures of palm oil and coconut oil. Typical synthetic detergents include alkyl sulfates and sulfonates having alkyl groups of from about 8 to about 18 carbon atoms, such as, for example, sodium lauryl sulfate, the sulfated fatty alcohols derived from coconut oil and palm oil. The soaps typically comprise up to about 5 percent by weight of the dentifrice composition.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine, APM (aspartylphenylalanine, methyl ester), saccharine and the like. Suitably, flavor and sweetening agents may together comprise from about 0.1 percent to 5 percent of the preparation.

Toothpastes, creams and gels typically contain a natural or synthetic thickener or gelling agent in proportions of from about 0.1 to about 10 percent, preferably from about 0.5 to about 5 percent by weight. Suitable gelling or thickening agents include for example, water-soluble salts of cellulose ethers such as sodium carboxymethyl cellulose and sodium carboxymethyl hydroxyethyl cellulose; natural gums such as gum karaya, gum arabic, and gum tragacanth; and colloidal magnesium aluminum silicate or finely divided silica.

Suitable humectants which may be employed in compositions of the invention include glycerine, propylene glycol, sorbitol, polypropylene glycol and/or polyethylene glycol and other polyhydric alcohols. The humectants may comprise from about 10 to 90 percent by weight of the dentifrice composition.

The invention will be further clarified by a consideration of the following examples, which are intended to be purely exemplary of the present invention.

GENERAL EXPERIMENTAL

Preparation of Stock Solutions 0.0045 M CPC. A 0.0045 M solution of cetylpyridinium chloride (CPC) was prepared by adding 0.3222±0.0001 g of CPC (Aldrich Chemical Co., Inc.) to a 200 mL volumetric flask and diluting to the mark with water. The final pH was approximately 6.9.

0.0045 M phytic acid. A 0.0045 M solution of phytic acid was prepared by adding 0.5847±0.0001 g of phytic acid (50 percent by weight, Jonas Chemical Co.) to a 100 mL volumetric flask and diluting to the mark with water. The pH of this solution was approximately 2.5.

0.0045 M Cu-phytic acid. A 0.0045 M solution of phytic acid and copper metal ion was prepared by adding 0.2042±0.0001 g of D-gluconic acid, CU(II) salt, (Aldrich Chemical Co., Inc.) to a 60 mL beaker. To this was added 0.5847±0.0001 g of 50% by weight phytic acid (Jonas Chemical Co.) and approximately 20 mL of water. This solution was transferred to a 100 mL volumetric flask and diluted to the mark with water. The final pH was approximately 3.0.

1.5 M sodium phosphate. A 1.5 M solution of sodium phosphate was prepared by adding 20.70±0.01 g of $NaH_2PO_4 \bullet H_2O$ (J. T. Baker Co.) to a beaker and dissolving in approximately 40 mL of water. The pH of this solution was adjusted to approximately 6.3 with the dropwise addition of 25 percent by weight sodium hydroxide solution. This solution was then transferred quantitatively to a 100 mL volumetric flask and diluted to the mark with water.

1.5 M sodium bicarbonate. A 1.5 M bicarbonate solution was prepared by adding 16.6±0.01 g of $NaHCO_3$ (J. T. Baker Co.) to a 100 mL volumetric flask and diluting to the mark with water. The pH of the sodium bicarbonate solution was approximately 8.4.

Glycolysis pH Test

A sucrose solution was prepared by loading 1.0 g of sucrose (Imperial Pure Cane Sugar) into a 60 mL beaker and then adding 20 mL of water. To this solution was added 8.0 mL of pooled whole human saliva. The saliva was collected from donors who had been permitted to eat or drink anything prior to the collection period, but had foregone any oral hygiene on the day of collection. Prior to the collection, each donor rinsed their mouth for thirty seconds with approximately 30 mL water, and after waiting about 5 minutes, began collecting saliva for 30–40 minutes, keeping the collected saliva on ice.

To the saliva/sucrose solution was added 1.0 mL of brain/heart infusion broth containing *Streptococcus mutants* (American Type Culture Collections No. 25175, ATCC) and 1.0 mL of brain/heart infusion broth containing *Streptococcus sanguis* (ATCC #10556). These cultures had been inoculated into 40 mL of broth and grown at 37° C. for sixteen hours prior to adding to the saliva/sucrose solution. (Each broth contained approximately 60 million colony forming units at the time of addition.)

Aliquots of 0.75 mL of the above saliva/sucrose/bacterial solution were added to the test tubes containing various washed HAP suspensions. These test tubes were capped and attached to a tube rotator and placed in a 37° C. incubator for sixteen hours. Following this incubation period, the rotator was removed from the oven and allowed to cool to ambient temperature. The pH of the solutions were checked with a pH meter using a pH electrode calibrated with pH 4, 7 and 10 buffers. The pH of each test tube was recorded and plotted in graphic format.

Treating and Washing Hydroxyapatite

To determine the substantivity of phytic acid and CPC either alone or in combination with copper ions, the following washing procedure of the hydroxyapatite was done prior to performing a glycolysis pH test:

A 60 mL beaker was loaded with 6.0 g of hydroxyapatite (HAP) in a buffer suspension (25 percent by weight solids from Sigma Chemical Co.) and washed with 30 mL of water. The HAP suspension was filtered through a medium glass fitted filter to obtain a HAP filter cake. The white solid filter cake containing 1.5 g of HAP was transferred to a dry 60 mL beaker and the total weight brought up to 15 grams with water to produce a 100 mg HAP/ML suspension.

Two mL of the HAP suspension was transferred to each of several sterile-disposable polystyrene 5 mL test tubes labeled $D_1-D_n$ (where n = identity number of the test solution). Four mL of a test solution were then added to each test tube. The tubes containing the HAP and test solution were capped and attached to a Tube Rotator and rotated end-over-end to allow the test solutions to contact the HAP for a total of ten minutes.

After mixing, the test tubes were placed in an Industrial Equipment Company (IEC) model K centrifuge and spun at setting 25 (mid-range) for ten minutes. The tubes were removed and the liquid layer decanted. A macropipettor was then used to add 3.0 mL of water to each test tube containing the centrifuged hydroxyapatite. The HAP solids were resuspended by vigorous in-and-out flowing action through the pipette and then placed on an end-over-nd rotator for ten minutes. The tubes were again centrifuged at setting 25 for ten minutes and the liquid layer decanted.

Following the three milliliter wash step, the HAP solids were resuspended in 4.0 mL of water. Two separate 0.5 mL samples (containing 25 mg HAP) of each HAP suspension was removed from each test suspension and placed in test tubes labeled $A_1-A_n$ or $A_1'-A_n'$ for the duplicate samples. A group of samples each contain one-eighth of the original treated HAP suspension which has been washed with three milliliters of water.

The remaining 3.5 mL in test tubes labeled $D_1-D_n$ were centrifuged for ten minutes, the test tubes removed, and the liquid layer decanted. Three milliliters of water were added to these test tubes and the HAP solids resuspended/washed using disposable pipettes. The tubes were centrifuged for ten minutes, the tubes removed and the liquid layer decanted. An additional three milliliters of water were added to these tubes and the HAP solids resuspended/washed by pipette. These tubes were again placed in the centrifuge and spun for ten minutes. The tubes were removed, the liquid layer decanted and 3.0 mL of water added to each tube. The HAP solids were resuspended and a 0.5 mL sample removed and placed in each of several 5 mL polystyrene test tubes labeled $B_1-B_n$ or $B_1'-B_n'$. These samples contained approximately 25 mg HAP solids which had been treated with test solution and then washed with a total of 13 milliliters of water.

The procedure given above was repeated a third and fourth time to create a series of test tubes labeled $C_1-C_N$ or $C_1'-C_n'$ and $D_1-D_n$ or $D_1'-D_N'$, with the exception that after the second three milliliter wash to give the C samples, the HAP was resuspended in 2 mL of water and for the D samples, 1 mL of water. The C and C' samples contained approximately 25 mg of HAP solids which had been treated with test solution and then washed with a total of 21 mL of water. The D and D' samples contained approximately 25 mg of HAP solids which had been treated with the test solution and then washed with a total of 31 mL water.

A glycolysis pH test was then performed as described above by adding 0.75 mL aliquots of the saliva/sucrose/bacterial mixture to the test tubes labeled $A_1-D_n$, each containing 0.5 mL of the treated washed HAP suspension. The $A_1'-D_n'$ samples were duplicates that could be tested for deodorizing power.

Measurement of deodorizing power

The ability of the oral compositions to reduce malodor was determined by placing 2 mL of the composition in a sample tube and bubbling a standard mixture of hydrogen sulfide ($H_2S$) and methyl mercaptan ($CH_3SH$) through the test solution for 1 minute and measuring the reduction of the $H_2S/CH_3SH$.

The $H_2S$ (542 ng/min) and $CH_3SH$ (735 ng/min) standards were obtained from permeation tube standards (Thermedics Inc.) and carried through the test samples by a 30 ml/min flow of nitrogen. The testing apparatus was fitted with a tee to allow diversion of a portion of the gas stream from the standards to obtain a linear response by the detector. The gas stream from the sample tube was analyzed using a Hewlett Packard 5890A gas chromatograph equipped with a flame photometric detector and a 11 meter $\times$ 0.125 cm (i.d.) fluorinated ethylene propylene teflon column packed with 5 percent polyphenyl (6 ring) ether and 0.5 percent phosphonic acid on a 40/60 mesh chromosorb T. The samples were chromatographed isothermally at 80° C. with the flame photometric detector at 130° C. using an ultra pure air gas flow of 30 ce/min.

EXAMPLE 1

To determine the ability of the copper ion to remove malodor components in the presence of phytic acid, the following compositions were tested as described for measuring deodorizing power:

(A) water (control)
(B) copper (II) acetate, (control);
(C) copper (II) gluconate, (control);
(D) copper (II) acetate and phytic acid; and
(E) copper (II) gluconate and phytic acid.

All samples were 0.0015 M prepared in 0.05 M phosphate at about pH 7.0

The 0.0015 M solutions of copper acetate and copper gluconate (Aldrich Chemical Co.) were prepared by adding 0.029 g and 0.068 g respectively to 100 mL of water. Samples D and E were prepared by adding 0.029 g of copper acetate or 0.068 g of copper gluconate to 100 mL of a 0.0015 M solution of phytic acid, prepared by diluting a 0.0045 M stock solution, and stirring until all the solids disappeared. The results of this evaluation are summarized in Table 1.

TABLE I

| Sample Nos. | Composition | pH | BLANK $H_2S$ | BLANK $CH_3SH$ | COMPOSITION $H_2S$ | COMPOSITION $CH_3SH$ | % REDN. $H_2S$ | % REDN. $CH_3SH$ |
|---|---|---|---|---|---|---|---|---|
| A | $H_2O$ | 7 | 17.1 | 25.4 | 11.1 | 17.1 | 35% | 33% |
| B | $Cu(OAc)_2$* | 7.04 | 16.9 | 25.1 | 1.7 | 4.8 | 90% | 81% |
| C | Cu(II)Gluconate* | 6.85 | 16.5 | 25.2 | 1.7 | 4.6 | 90% | 82% |
| D | $Cu(OAc)_2$/Phytic acid | 7.08 | 16.7 | 24.9 | 1.7 | 4.7 | 90% | 81% |
| E | Cu(II)Gluconate/Phytic acid | 6.8 | 15.7 | 24.9 | 1.7 | 4.4 | 89% | 82% |

*evaluation was performed immediately after the preparation of the composition as a precipitate forms after 2-3 hours following the sample preparation.

The results show that in the presence of an anionic buffer, the copper ion and phytic acid both remain in solution and that the phytic acid does not interfere with the ability of copper to remove hydrogen sulfide or methyl mercaptan from a gas stream.

EXAMPLE 2

The ability of Cu-phytic acid to adsorb to a hydroxyapatite surface and retain deodorizing power was measured by treating 1 mL of a hydroxyapatite (HAP) suspension with 1 mL of a test solution and then subjecting the HAP to several washing steps.

The HAP suspension was prepared by washing a 24.5 g portion of HAP (Sigma Chemical Co., 24.5 percent solids in phosphate buffer, 0.001 M, pH 6.8) with three 30 mL portions of water. The washed hydroxyapatite powder (approximately 6 g) was then suspended in 60 mL of water with vigorous stirring to give a 100 mg/ml homogeneous white HAP suspension.

The test solutions were as follows: Solution A: 0.0015 M copper acetate, 0.0015 M phytic acid and 0.05 M phosphate buffer at pH 6.8; Solution B: 0.0015 M copper acetate and 0.05 M phosphate buffer at pH 7.05; Solution C: water (control).

Solutions A and B were prepared as described in Example 1 and the solutions filtered through a 0.22 micron syringe filter immediately before use.

Into separate tubes labeled 1, 2, and 3 were added 1 mL of the HAP suspension and into tube 1, one mL of solution A; into tube number 2, one mL of solution B; and into tube number 3, one mL of solution C. The tubes were immediately capped and placed on an end-over-end rotator for 5 minutes. The suspensions were then centrifuged in a IEC HN-SII table top model centrifuge at full speed (4,000 rpm). The supernatant from each tube was removed and 3.0 mL of water added and the solids suspended by vigorous pipette action. The suspensions were then centrifuged again as above and the supernatant discarded. The solids were then washed with 3 mL portions of water in this manner an additional three times so the total water wash volume was 12 mL (from 4 three-ml washes). After the last wash the supernatant was removed and the moist solid washed HAP samples were suspended in two mL of phosphate buffer (0.05 M, pH 7.0) and their ability to deodorize was performed as described under general experimental. The results of this evaluation are given in Table II.

TABLE II

| Sample Nos. | BLANK $H_2S$ | BLANK $CH_3SH$ | TEST SOLN. $H_2S$ | TEST SOLN. $CH_3SH$ | Percent REDN. $H_2S$ | Percent REDN. $CH_3SH$ |
|---|---|---|---|---|---|---|
| 1[a] | 17 | 25.1 | 1.7 | 4.4 | 90% | 83% |
| 2[b] | 15.3 | 22.6 | 1.8 | 5.2 | 88% | 77% |
| 3[c] | 17.2 | 26 | 6.3 | 12.5 | 63% | 42% |

[a]HAP treated with copper acetate, phytic acid and phosphate
[b]HAP treated with copper acetate and phosphate
[c]HAP washed with water The results show that the presence of phytic acid and a phosphate buffer does not interfere with the ability of Copper (II) to be adsorbed onto hydroxyapatite and to adsorb volatile sulfur compounds.

EXAMPLE 3

The following compositions were evaluated for retention on a HAP surface after washing as measured by the ability of the treated and washed HAP to reduce malodor and inhibit microorganisms:

Sample 1: water;
Sample 2: cetylpyridinium chloride;
Sample 3: 0.0015 M $Cu^{++}$ metal ion, phytic acid, phosphate buffer and cetylpyridinium chloride;
Sample 4: 0.00021M $Cu^{++}$ metal ion, phytic acid, phosphate buffer and cetylpyridinium chloride;
Sample 5: phytic acid, phosphate buffer and cetylpyridinium chloride.

The cetylpyridinium chloride and phytic acid being at a concentration of 0.0015 M and phosphate at 0.5 M.

All samples were prepared by mixing the appropriate amount of required stock solutions and diluting with water when necessary to give the indicated concentrations. The $Cu^{++}$ metal ion, phytic acid and phosphate buffer were mixed and adjusted to approximately pH 6.9 with 1.0 N sodium hydroxide prior to the addition of cetylpyridinium chloride.

These solutions were used to treat hydroxyapatite powder which was then washed according to procedure listed in General Experimental. One set of the split hydroxyapatite samples ($A_1$-$A_n$, $B_1$-$B_n$, etc.) along with their water and cetylpyridinium chloride controls were subjected to the glycolysis test to give the results in Table III.

TABLE III

| mL of Water Wash | pH of Washed Samples After Incubation* 1 | 2 | 3 | 4 | 5 |
|---|---|---|---|---|---|
| 3 | 5.07 | 7.43 | 7.48 | 7.12 | 7.57 |
| 13 | 5.1 | 5.62 | 7.38 | 7.45 | 7.62 |
| 21 | 5.13 | 5.09 | 7.48 | 7.52 | 7.64 |

TABLE III-continued

| mL of Water Wash | pH of Washed Samples After Incubation* | | | | |
|---|---|---|---|---|---|
| | 1 | 2 | 3 | 4 | 5 |
| 31 | 5.16 | 5.18 | 7.38 | 7.56 | 7.67 |

*Sample 1 = Water
Sample 2 = Cetylpyridinium chloride
Sample 3 = 0.0015 M copper (II), phytic acid, phosphate and cetylpyridinium chloride
Sample 4 = 0.00021 M copper (II), phytic acid, phosphate and cetylpyridinium chloride
Sample 5 = phytic acid, phosphate and cetylpyridinium chloride The second set of the split hydroxyapatite samples ($A_1'-A_n'$, $B_1'-B_n'$, etc.) were suspended in 2.0 mL of phosphate buffer and evaluated by the procedure given in measurement for deodorizing power described under general experimental. The results are shown in Table IV.

TABLE IV

| | AMOUNT OF $H_2S/CH_3SH$ (ng/10 mL of $N_2$) | | |
|---|---|---|---|
| Sample | BLANK | TEST SOLUTION | % REDUCTION |

| Nos.* | $H_2S$ | $CH_3SH$ | $H_2S$ | $CH_3SH$ | $H_2S$ | $CH_3SH$ |
|---|---|---|---|---|---|---|
| 3 | 15.4 | 23.7 | 2.3 | 7.7 | 85% | 68% |
| 4 | 13.7 | 24.6 | 5.3 | 14.4 | 61% | 41% |
| 5 | 15.4 | 25 | 8.1 | 14.6 | 47% | 42% |

*Sample 3 = 0.0015 M copper (II), phytic acid, phosphate and cetylpyridinium chloride
Sample 4 = 0.0021 M copper (II), phytic acid, phosphate and cetylpyridinium chloride
Sample 5 = phytic acid, phosphate and cetylpyridinium chloride These results indicate that the addition of copper/phytic acid to CPC enhances the substantivity of CPC to hydroxyapatite to the same degree as phytic acid alone. These results also show that the addition of copper to a mixture of phytic acid/CPC improves their ability to remove volatile sulfur compounds from a gas stream while adsorbed on a hydroxyapatite surface.

EXAMPLE 4

The ability of phytic acid to enhance the substantivity of an antimicrobial to HAP was measured by treating HAP with a test solution, washing the HAP as described under general experimental and measuring retention of antimicrobial activity by the glycolysis pH test described above.

The HAP was treated with the following test solutions:

A. Water (control);
B. cetylpyridinium chloride (CPC);
C. phytic acid, phosphate (PaP);
D. $Cu^{++}$ metal ion, phytic acid, phosphate buffer (Cu-PaP);
E. phytic acid, phosphate buffer and cetylpyridinium chloride (PaPC);
F. metal ion, phytic acid, phosphate buffer and cetylpyridinium chloride (Cu-PaPC).

The cetylpyridinium chloride and phytic acid concentration being 0.0015 M, phosphate 0.5 M and copper ion 0.5 millimolar.

Samples B, C and E were prepared by mixing the appropriate amount of required stock solutions and diluting with water when necessary to give the indicated concentrations.

Sample D was prepared by placing 0.0102 g of D-gluconic acid, CU(II) salt, into a jar and dissolving with the addition of 15 mL of a 0.0045 M phytic acid solution. Fifteen mL of a 1.5 M phosphate buffer solution was added to the jar and the pH adjusted to about 7 with the dropwise addition of a 50 percent sodium hydroxide solution. A 15 mL aliquot of water was then added to give the final concentrations listed above. For Sample F, a 15 mL aliquot of a 0.0045 M cetylpyridinium chloride solution was used to replace the final water addition as described for sample D.

The results of this substantivity trial are given in Table V.

TABLE V

| Volume of wash (mL) | pH AS A FUNCTION OF HAP WASHINGS | | | | | |
|---|---|---|---|---|---|---|
| | SAMPLES | | | | | |
| | Water | $CPC^a$ | $PaP^b$ | $Cu-PaPC^c$ | $PaPC^d$ | $Cu-PaPC^e$ |
| 3 | 5.02 | 7.64 | 5.21 | 5.25 | 7.60 | 7.16 |
| 13 | 5.06 | 5.53 | 5.13 | 5.24 | 7.64 | 7.48 |
| 21 | 5.06 | 5.12 | 5.11 | 5.27 | 7.66 | 7.57 |
| 21 | 5.15 | 5.14 | 5.15 | 5.32 | 7.71 | 7.59 |

$^a$CPC = cetylpyridinium chloride (Control);
$^b$PaP = phytic acid and phosphate (Control);
$^c$Cu—PaP = copper (II), phytic acid and phosphate (Control);
$^d$PaPC = phytic acid, phosphate and cetylpyridinium chloride;
$^e$Cu—PaPC = Copper (II), phytic acid, phosphate and cetylpyridinium chloride The results show that phytic acid enhances the substantivity of cetylpyridinium chloride to the HAP and that copper phytate without CPC is ineffective. In addition, the results show that the addition of copper does not interfere with the substantivity enhancement of CPC with phytic acid. Increasing the copper ion concentration to 0.0015 M did not alter the improved substantivity of CPC in the presence of phytic acid.

EXAMPLE 5

In this trial, the preparation of HAP and the treatment of HAP with the test solutions were as previously described under general experimental. The following solutions were tested for HAP substantivity as measured by the glycolysis pH test:

A. Water (control);
B. cetylpyridinium chloride (CPC);
C. copper ion, phytic acid, sodium bicarbonate (Cu-PaB);
D. cetylpyridinium chloride, sodium bicarbonate (CPCB);
E. N-tetradecyl-4-ethylpyridinium bromide (TDEP);
F. copper ion, phytic acid, sodium bicarbonate, cetylpyridinium chloride (Cu-PaBC);
G. phytic acid, sodium bicarbonate, cetylpyridinium chloride (PaBC);
H. copper ion, phytic acid, sodium bicarbonate, N-tetradecyl-4-ethylpyridinium bromide (Cu-PaBT).

The concentration of the components being 0.0015 M except sodium bicarbonate at 0.5 M.

Solutions B, C, D, 1 and 2 were prepared by mixing the appropriate amount of stock solutions and diluting with water when necessary to give the indicated concentrations.

Sample E was prepared by adding 0.0173±0.0001 g of N-tetradecyl-4-ethylpyridinium bromide to a 10 mL volumetric flask and diluting to mark with water. A 4 mL aliquot of this 0.0045 M solution was diluted with 8 mL of water to produce a final concentration of 0.0015 molar N-tetradecyl-4-ethylpyridinium bromide.

Sample 3 was prepared by adding a 4 mL aliquot of 1.5 M sodium bicarbonate to 4 mL of a 0.0045 M Cu++/phytic acid stock solution and then adding 4 mL of a 0.0045 M N-tetradecyl-4-ethylpyridinium bromide stock solution. The pH of this formulation was about 8.3.

The results from this trial are given in Table VI.

TABLE VI

| VOLUME OF WASH (mL) | pH AS A FUNCTION OF HAP WASHINGS Samples | | | | | | |
|---|---|---|---|---|---|---|---|
| | Water | CPC[1] | CuPaB[2] | CPCB[3] | ETDP[4] | Cu—PaBC[5] | PaBC[6] | Cu—PaBT[7] |
| 3 | 5.23 | 7.71 | 8.01 | 8.78 | 7.82 | 8.62 | 8.78 | 8.73 |
| 13 | 5.27 | 7.80 | 6.05 | 8.53 | 5.42 | 8.36 | 8.50 | 8.39 |
| 21 | 5.30 | 6.73 | 5.82 | 5.73 | 5.32 | 8.23 | 8.37 | 8.26 |
| 31 | 5.34 | 5.43 | 5.84 | 6.05 | 5.39 | 8.19 | 8.25 | 8.14 |

[1]CPC = cetylpyridinium chloride (CPC);
[2]CuPaB = copper, phytic acid and sodim bicarbonate;
[3]CPCB = cetylpyridinium chloride and sodim bicarbonate;
[4]ETDP = N-tetradecyl-4-ethylpyridinium bromide
[5]Cu—PaBC = copper, phytic acid, sodim bicarbonate and cetylpyridinium chloride;
[6]PaBC = phytic acid, sodim bicarbonate, and cetylpyridinium chloride;
[7]Cu—PaBT = copper, phytic acid, sodim bicarbonate and 4-ethyltetradecylpyridinium bromide The results show that sodium bicarbonate buffer works as effectively in combination with phytic acid and cetylpyridinium chloride as does the phosphate buffer. In addition N-tetradecyl-4-ethylpyridinium bromide works as well as cetylpyridinium chloride as an antimicrobial in combination with phytic acid, copper and bicarbonate buffer.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. An oral composition consisting essentially of: (a) from about 0.0002 to about 1 percent by weight of one or more copper salts; (b) from about 0.0001 to about 10 percent by weight of one or more compounds having C-O-P bonds wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (c) from about 0.001 to about 10 percent by weight of one or more cationic antimicrobial compounds; (d) from about 0.1 to about 20 percent by weight of one or more a compatibilizing agents; and (e) balance, an orally acceptable vehicle, having a pH in the range of about 4.5 to about 9, wherein the compatibilizing agent prevents precipitation of the compounds having C-O-P bonds, antimicrobial compound and copper salt when in an aqueous environment and the compatibilizing agent allows compounds having C-O-P bonds to enhance retention of the cationic antimicrobial compound to a surface containing hydroxyapatite.

2. The oral composition of claim 1 wherein the compound having C-O-P bonds is myo-inositol hexakis(dihydrogen phosphate) or a physiologically acceptable salt thereof.

3. The oral composition of claim 1 wherein the copper salt is copper acetate, copper gluconate, copper sulfate, copper chloride, copper citrate, copper succinate, copper tartrate or mixtures thereof.

4. The oral composition of claim 3 wherein the copper salt is copper gluconate or copper acetate.

5. The oral composition of claim 1 wherein the molar ratio of cupric ion to compound having C-O-P bonds is from about 1:100 to about 1:1.

6. The oral composition of claim 1 wherein the cationic antimicrobial compound is one or more quaternary ammonium compounds selected from the group consisting of formula I

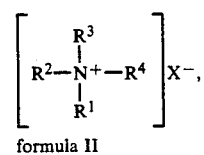

formula II

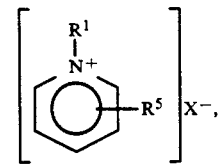

and a mixture thereof;
wherein
$R^1$ is a $C_8$-$C_{20}$ alkyl,
$R^2$ is benzyl or $C_1$-$C_{12}$ alkyl,
$R^3$ and $R^4$ are independently a $C_1$-$C_7$ alkyl or -(CH$_2$—CHOH—CH$_2$—O)$_n$H wherein n is an integer from 1 to 6,
$R^5$ is -H, a $C_1$-$C_7$ alkyl or -(CH$_2$—CHOH—CH$_2$—O)$_n$H wherein n is an integer from 1 to 6, and
$X^-$ is chloride, bromide, iodide or fluoride.

7. The oral composition of claim 1 wherein the compatibilizing agent is an anionic buffer.

8. The oral composition of claim 7 wherein the anionic buffer is phosphate, acetate, borate, citrate, bicarbonate, gluconate, tartrate, sulfate or mixtures thereof.

9. The oral composition of claim 6 wherein the anionic buffer is phosphate, bicarbonate or a mixture thereof.

10. The oral composition of claim 9 wherein the cationic antimicrobial compound is a quaternary ammonium compound represented by Formula II as defined in claim 6.

11. The oral composition of claim 10 wherein the quaternary ammonium compound is cetylpyridinium chloride.

12. The oral composition of claim 10 wherein the quaternary ammonium compound is N-tetradecyl-4-ethylpyridinium chloride.

13. The oral composition of claim 7 wherein the copper salt is copper gluconate, copper acetate or a mixture thereof, the quaternary ammonium compound is cetylpyridinium chloride and the compound having C-O-P bonds is myo-inositol hexakis(dihydrogen phosphate) or a physiologically acceptable salt thereof.

14. The oral composition of claim 1 wherein the cationic antimicrobial compound is a quaternary ammonium compound represented by formula II as defined in claim 6.

15. The oral composition of claim 14 wherein the quaternary ammonium compound is cetylpyridinium chloride.

16. The oral composition of claim 14 wherein the quaternary ammonium compound is N-tetradecyl-4-ethylpyridinium chloride.

17. A method of inhibiting oral malodor in mammals comprising administering to the oral cavity an oral composition consisting essentially of: (a) from about 0.0002 to about 1 percent by weight of one or more copper salts; (b) from about 0.001 to about 10 percent by weight of one or more compounds having C-O-P bonds wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (c) from about 0.001 to about 10 percent by weight of one or more cationic antimicrobial compounds; (d) from about 0.1 to about 20 percent by weight of one or more a compatibilizing agents; and (e) balance, an orally acceptable vehicle having a pH in the range of about 4.5 to about 9, wherein the compatibilizing agent prevents precipitation of the compounds having C-O-P bond, antimicrobial compound and copper salt when in an aqueous environment and the compatibilizing agent allows compounds having C-O-P bonds to enhance retention of the cationic antimicrobial compound to a surface containing hydroxyapatite.

18. The method of claim 17 wherein the compound having C-O-P bonds is myo-inositol hexakis(dihydrogen phosphate) or a physiologically acceptable salt thereof.

19. The method of claim 17 wherein the copper salt is copper acetate, copper gluconate, copper sulfate, copper chloride, copper citrate, copper succinate, copper tartrate or mixtures thereof.

20. The method of claim 19 wherein the copper salt is copper gluconate, copper acetate or a mixture thereof.

21. The method of claim 17 wherein the molar ratio of cupric ion to compound having C-O-P bonds is about 1:100 to about 1:1.

22. The method of claim 17 wherein the cationic antimicrobial compound is one or more quaternary ammonium compounds selected from the group consisting of Formula I

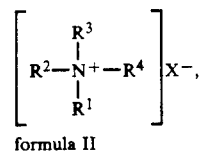

formula II and a mixture thereof;
wherein
$R^1$ is a $C_8-C_{20}$ alkyl,
$R^2$ is benzyl or $C_1-C_{12}$ alkyl,

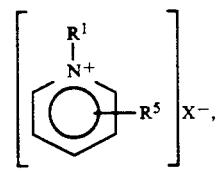

$R^3$ and $R^4$ are independently a $C_1-C_7$ alkyl or -$(CH_2-CHOH-CH_2-O)_nH$ wherein n is an integer from 1 to 6,
$R^5$ is -H, a $C_1-C_7$ alkyl or -$(CH_2-CHOH-CH_2-O)_nH$ wherein n is an integer from 1 to 6, and
$X^-$ is chloride, bromide, iodide or fluoride.

23. The method of claim 17 wherein the compatibilizing agent is an antionic buffer.

24. The method of claim 23 wherein the anionic buffer is phosphate, acetate, borate, citrate, bicarbonate, gluconate, tartrate, sulfate or mixtures thereof.

25. The method of claim 24 wherein the anionic buffer is phosphate, bicarbonate or a mixture thereof.

26. The method of claim 25 wherein the copper salt is copper gluconate, copper acetate or a mixture thereof, the quaternary ammonium compound is cetylpyridinium chloride and the compound having C-O-P bonds is myo-inositol hexakis(dihydrogen phosphate) or a physiologically acceptable salt thereof.

27. The method of claim 22 wherein the quaternary ammonium compound is represented by Formula II as defined in claim 19.

28. The method of claim 27 wherein the quaternary ammonium compound is cetylpyridinium chloride.

29. The method of claim 27 wherein the quaternary ammonium compound is N-tetradecyl-4-ethylpyridinium bromide.

30. A process for preparing an oral composition as defined in claim 1 comprising the steps of
(a) dissolving the metal salt, phytic acid and compatibilizing agent in water, and
(b) dissolving the cationic antimicrobial compound or cationic antimicrobial solution in the solution obtained from step a;
wherein the pH of the oral composition is adjusted to between about 6 and about 8 prior to or after the addition of the cationic antimicrobial compound or cationic antimicrobial solution.

31. A kit for controlling oral malodor comprising one or more copper salts in an orally-acceptable vehicle, one or more compounds having C-O-P bonds wherein the compound having C-O-P bonds is myo-inositol hexakis(dihydrogen phosphate), myo-inositol tetrakis(dihydrogen phosphate), myo-inositol pentakis(dihydrogen phosphate) or physiologically acceptable salts thereof, one or more compatibilizing agents in an orally-acceptable vehicle, and a cationic antimicrobial compound in an orally-acceptable vehicle; and a means to contain the compound having C-O-P bonds separate from the cationic antimicrobial compound.

* * * * *